United States Patent [19]
Bloink et al.

[11] Patent Number: 5,762,737
[45] Date of Patent: Jun. 9, 1998

[54] POROUS CERAMIC AND PROCESS THEREOF

[75] Inventors: Raymond Leo Bloink, Swartz Creek; James Thompson Young, Fenton, both of Mich.

[73] Assignee: General Motors Corporation, Detroit, Mich.

[21] Appl. No.: 717,589

[22] Filed: Sep. 25, 1996

[51] Int. Cl.$^6$ ........................................... C04B 38/06
[52] U.S. Cl. ............................ 156/89; 264/44; 264/618
[58] Field of Search ......................... 264/44, 618; 156/89

[56] References Cited

U.S. PATENT DOCUMENTS

| | | | |
|---|---|---|---|
| 3,007,222 | 11/1961 | Ragan | 25/156 |
| 4,508,841 | 4/1985 | Onuma et al. | 264/44 |
| 4,943,330 | 7/1990 | Iino et al. | 156/89 |
| 5,329,806 | 7/1994 | McClanahan et al. | 73/31.05 |
| 5,360,528 | 11/1994 | Oh et al. | 204/425 |
| 5,384,030 | 1/1995 | Duce et al. | 204/426 |
| 5,467,636 | 11/1995 | Thompson et al. | 73/23.31 |
| 5,518,603 | 5/1996 | Furuhashi et al. | 204/429 |
| 5,522,979 | 6/1996 | Tatumoto et al. | 204/429 |

OTHER PUBLICATIONS

Function and Design of $ZrO_2$ Exhaust Oxygen Sensors; Chapter 2; pp. 2-1-2-7.

Air-Fuel Ratio Sensor Utilizing Ion Transportation in Zirconia Electrolyte; T. Sasayama & T. Yamauchi, Hitachi America., Ltd; Robert Byers, Hitachi Farmington Hills Tech. Center S. Suzuki & S. Ueno, Hitachi Ltd.; No. 910501; pp. 169–175.

Tape Casting: The Basic Process for Meeting the Needs of Electronics Industry, Richard E. Mistler; Ceramic Bulletin, Col. 69, No. 6, 1990; pp. 1022–1026.

Tape Casting, Richard E. Mistler; Engineered Materials Handbook, vol. 4: Ceramics and Glasses; pp. 161–165.

Primary Examiner—James Derrington
Attorney, Agent, or Firm—Anthony Luke Simon

[57] ABSTRACT

A process for assembling a porous ceramic coating to a substrate comprising: forming a ceramic matrix tape including a first ceramic powder having a first full density sintering temperature, a second ceramic powder having a second full density sintering temperature and a fugitive filler material; placing the ceramic matrix tape on the substrate; and heating the ceramic matrix tape and substrate to a sintering temperature above the first full density sintering temperature and below the second full density sintering temperature, wherein the fugitive filler material decomposes during said heating.

10 Claims, 2 Drawing Sheets

POROUS CERAMIC AND PROCESS THEREOF

This invention relates to a porous ceramic and process thereof.

BACKGROUND OF THE INVENTION

Many oxygen and other gas sensors include a substrate such as an electrolytic material of a known type formed in a flat, thimble-like or tubular shape. The substrate typically includes electrodes on the exterior and interior thereof or fabricated using multi-layer ceramic technologies. It is desirable to protect the sensor substrate with a porous coating that allows the gas being sensed to pass through while preventing other gases or particulate material from reacting with the surface of the substrate. In certain types of sensors, it is desirable that the porous coating act as a diffusion barrier that limits the rate that gases can pass to or from the electrolyte substrate.

One known method for applying a porous coating includes flame spraying a spinel on the surface of the sensor substrate. In sensors that are flat shaped and fabricated using multi-layer ceramic technology, it is desirable to provide a porous coating that can be fabricated with the substrate itself, for example, as another ceramic layer sintered along with the layers of the sensor substrate so that the forming of the substrate and the porous coating are obtained in the same sintering process. Application of such coatings, however, create problems if the amount of shrinkage of the coating layers during the sintering is different from that of the substrate layers. If there is such a difference in shrinkage, stress can result between the different ceramic layers, giving rise to warping, cracking and/or peeling of the layers.

SUMMARY OF THE PRESENT INVENTION

It is an object of this invention to provide a porous ceramic according to claim 1.

Advantageously, this invention provides a porous ceramic material suitable for use on a substrate requiring a porous protective coating.

Advantageously, this invention provides a porous ceramic material suitable for use on a substrate comprising multiple electrolyte or ceramic layers and that can be co-sintered with the multiple layers.

Advantageously, this invention provides a porous ceramic material whose amount of shrinkage can be controlled to match that of the substrate on which it is applied.

Advantageously, this invention provides a porous ceramic material that can be formed into a ceramic tape and co-sintered with other ceramic bodies also provided in the form of ceramic tapes.

Advantageously, this invention provides a porous ceramic material suitable for use as a porous protective coating on an electrolyte or other substrate of a gas sensor or other gas diffusing apparatus.

Advantageously, the porous ceramic material provided by this invention achieves substantially uniform pore diameter on the order of 1 micron or less and has a porosity that is controllable to meet particular applications requirements.

Advantageously, this invention provides a ceramic material that is sintered at a predetermined sintering temperature. The ceramic material components include two ceramic powders, the first of which does not sinter to full density at the predetermined sintering temperature and the second of which does sinter to or near to full density at the predetermined sintering temperature. The ceramic material is made also using a fugitive filler with an average particle size of less than 1 micron that decomposes during the sintering cycle. The first ceramic powder resists shrinkage and the second ceramic powder increases shrinkage during firing. Thus, the ratio of the first and second ceramic powders are adjusted to adjust the amount of shrinkage that occurs on the part during sintering at the predetermined temperature. The fugitive filler material creates the pores as it decomposes during sintering, and the porosity of the ceramic is controllable by the amount of fugitive filler provided relative to the first and second ceramic powders.

Advantageously then, according to a preferred example of this invention, a porous ceramic material is provided comprising a matrix of first and second ceramic materials sintered at a temperature at or above the full density sintering temperature of the first ceramic material and less than the full density sintering temperature of the second ceramic material, wherein the matrix forms pores having a median pore size of less than 1 micron.

Advantageously then, according to another preferred example, this invention provides a process for producing a porous ceramic comprising the steps of providing a first ceramic powder having a first full density sintering temperature, providing a second ceramic powder having a second full density sintering temperature, providing a fugitive filler material, forming a green body from the first ceramic powder, the second ceramic powder and the fugitive material and heating the green body to a temperature between the first and second full density sintering temperatures wherein the green body is sintered into the porous ceramic.

BRIEF DESCRIPTION OF THE DRAWINGS

The present invention will now be described with reference to the following drawings in which.

DETAILED DESCRIPTION OF THE INVENTION

Figure 1:
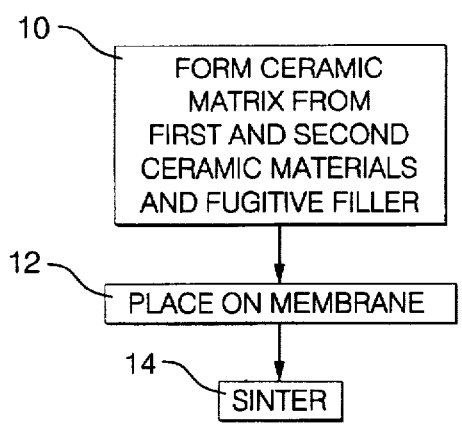
FIG. 1 illustrates an example process according to this invention.

In the following examples, the materials provided were tape cast from slurries prepared using a mixture of 60% MEK (methyl ethyl ketone) and 40% denatured ethanol. Emphos PS-21A phosphate ester dispersant, available from Witco Corporation, was predissolved in the solvent to give a typical loading of 1.7 weight percent based on the total weight of the solids to be added. Slurry batches of about 400 g and 61 weight percent solids were mixed in 0.5 gallon Nalgene containers filled almost half way with one inch round alumina media. Some variations to the examples included milling the oxides and filler material for two hours prior to binder and plasticizer additions. Poly (vinyl butyral) binder (Butvar B-98, available from Monsanto Corp.) at 11.8 weight percent was added along with butyl benzyl phthalate plasticizer (Santicizer 160, also available from Monsanto Corp.) at 7.1 weight percent based on the total weight of solids.

The containers were then shaken using a paint mixer for five minutes to help dissolve the binder. The slurries were milled at 110 rpm for an additional hour and then left to sit for about 16 hours without agitation. Before casting, the slurries were shaken for two minutes and given a final milling of at least one hour. After vacuum deairing, the slurries were cast on a membrane substrate such as non-coated mylar using a caster of a known type. Unless otherwise specified below, the tape was cast to a thickness of 0.010 inches. The material cast onto the mylar, but not yet sintered, is generally referred to as green tape or a green body (the mylar is removed before sintering).

In the following examples, the sintering temperature is 1510° C. and the sintering time is two hours. The fugitive filler material is Thermax carbon black powder from R.T. Vanderbilt Co., having an average particle size of less than one micron. The percent porosities below were determined using Hg porosimetry.

EXAMPLE 1

An alumina, A-152SG, available from Alcoa, which sinters to full density at about 1620° C., provides 20.2% of the powder volume. Premalox 10SG (from Alcoa Co., is another alumina with a smaller particle diameter, which sinters to full density at about 1500° C.) provides 60.7% of the powder volume and the fugitive filler provides 19.1% of the powder volume. The resulting tape when fired at the sintering temperature has a shrinkage of 14.4%, a uniform fine diameter interconnected pore structure with a median pore diameter of 0.32 microns and a percent porosity of 21.8.

EXAMPLE 2

The low reactivity powder is a milled, partially stabilized zirconia body, prepared from pre-fired zirconia, for example, a body made using SC30S from Magnesium Elektron, Inc., prefired at 1450° C., having a full density sintering temperature of about 1600° C. The low reactivity powder provides 40.4% of the powder volume. The high reactivity powder is a milled, partially stabilized zirconia body prepared, for example, using SC30S, having a full density sintering temperature of about 1500° C. and provides 40.5% of the powder volume. The fugitive filler provides 19.1% of the powder volume.

The tape shrank 16.5% during firing, provided a highly uniform, fine, interconnected pore structure with a median pore diameter of 0.39 microns and had a percent porosity of 20.7.

EXAMPLE 3

The low reactivity powder is the A-152SG alumina providing 31.1% of the powder volume. The high reactivity powder is a milled partially stabilized zirconia body, for example a body made using ZR2, available from SEPR Corp., having a full density sintering temperature of about 1500° C., and provides 49.8% of the powder volume. The fugitive filler provides 19.1% of the powder volume. The resulting tape shrank 15.8% during firing, yielded a substantially uniform and interconnected pore structure with a median pore diameter of 0.39 microns and had a porosity percentage of 20.8.

The examples 1-3 illustrate that the invention can be implemented using alumina compounds (Example 1), zirconia compounds (Example 2), or a mixture of compounds (Example 3).

In Examples 4-11, the low reactivity powder is the A-152SG alumina, the high reactivity powder is the zirconia body made using ZR2 and the fugitive filler is the carbon black.

EXAMPLE 4

The low reactivity powder is provided at 1 part (by volume) for every 0.9 parts (by volume) of high reactivity powder and the carbon black provides 19% of the total powder volume. During sintering the shrinkage was 13.6% and the resulting porosity percentage is 23.2.

EXAMPLE 5

The low reactivity powder is provided at 1 part (by volume) for every 1.2 parts (by volume) of the high reactivity powder. The carbon black provides 19% of the total powder volume. The tape had a shrinkage during firing of 14.9% and a resulting percent porosity of 23.3.

EXAMPLE 6

The low reactivity powder is provided at 1 part (by volume) for every 1.7 parts (by volume) of the high reactivity powder. The carbon black provides 19% of the volume of the powders. The tape had 16.5% shrinkage during firing with a resulting porosity percentage of 17.9.

The examples 4-6 illustrate that by varying the ratio of low and high reactivity powders, the amount of shrinkage of the tape can be controlled. These examples illustrate how the ratio of low to high reactivity powders can be adjusted to match the shrinkage of the porous ceramic to an electrolyte or other substrate to which it is to be co-sintered.

EXAMPLE 7

The low reactivity powder is provided at 1 part (by volume) for every 0.9 parts (by volume) of high reactivity powder and the carbon black provides 19% of the total powder volume. During firing, the shrinkage was 13.6% and the resulting porosity percentage was 23.2.

Example green bodies according to this example were sintered onto a sensor structure, such as of the type set forth in U.S. Pat. Nos. 5,467,636, 5,384,030 and 5,329,806 and in pending U.S. patent application, Ser. No. 08/600,136. The green bodies are laminated to the sensor using an iso-static lamination process in which the sensor and green bodies were subjected to 2000 psi of pressure for five minutes at 80° C. The green bodies were then co-sintered with the sensor at 1510° C. for two hours. The resulting sensor was placed into a chamber in which it was exposed to internal combustion engine exhaust gases with additives to accelerate silica poisoning of the sensor. In that test, the sensor had a silica poison time of 270 minutes.

EXAMPLE 8

The low reactivity powder was provided at 1 part (by volume) for every 0.8 parts (by volume) of the high reactivity powder and the carbon black provided 27% of the total powder volume. During firing the percent shrinkage was 14.0% and the resulting percent porosity was 30.5. When sintered onto a sensor and subjected to the same silica poisoning test referred to in Example 7, the silica poison time was 150 minutes.

EXAMPLE 9

The low reactivity powder was provided at 1 part (by volume) for every 0.7 parts (by volume) of the high reactivity powder and the carbon black provided 35% of the total powder volume. The tape had a firing shrinkage of 14.1% with the resulting percent porosity of 36.2. When sintered onto a sensor and subjected to the silica poison test, the poison time was 96 minutes.

Examples 7–9 illustrate that the porosity of the porous coating can be controlled by adjusting the percentage of fugitive filler material used and also illustrate the inverse relationship between the porosity and resistance to silica poisoning.

EXAMPLE 10

The low reactivity powder is provided at 1 part (by volume) for every 0.9 parts (by volume) of the high reactivity powder and the carbon black is provided so that it comprises 19% of the total powder volume. The percent porosity achieved is 23.2 with a median pore diameter of 0.39 microns when cast in a tape having a thickness while green of 0.016 inches. With the tape used as a protective coating on an example oxygen sensor, the sensor had a silica poison time of 23.6 hours.

This example illustrates that the increased thickness of the example porous coating according to this invention increases the resistance of the sensor to silica poisoning.

Referring now to FIG. 1, the example process according to this invention starts at block 10 where the ceramic matrix comprising the high and low reactivity ceramic powders and the fugitive filler material is formed as described above. At block 12, the material is placed on a membrane, such as non-coated mylar, according to a conventional tape-casting procedure of a type known to those skilled in the art. Then, at block 14, the green body is sintered as described above.

Figure 2:
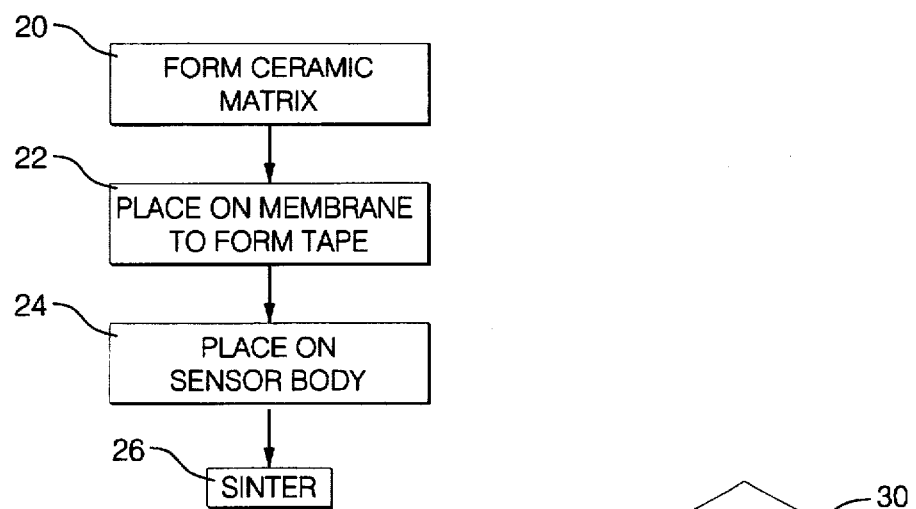
FIGS. 2 and 3 illustrates a second example process according to this invention.
Figure 3:
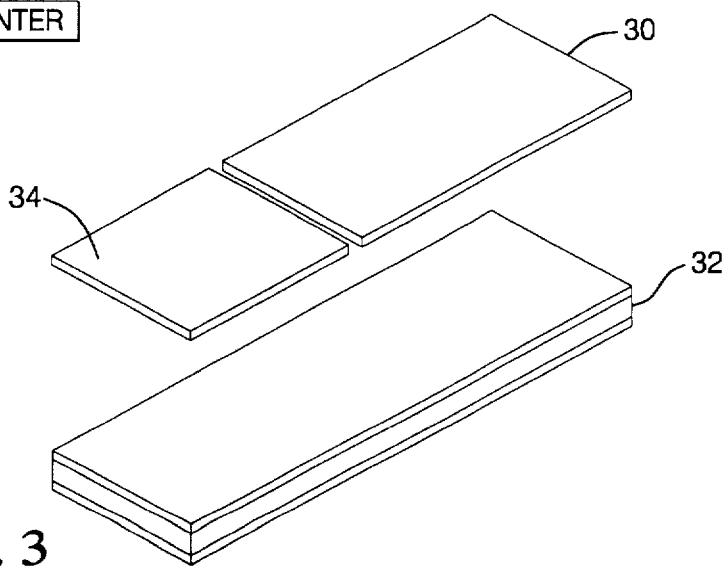

The sintering process is preferably a co-sintering in which the ceramic is sintered together with the electrolyte or other ceramic substrate to which the ceramic according to this invention is to be applied. Referring now to FIGS. 2 and 3, this process begins at block 20, where a ceramic matrix as described according to any of the above examples is formed. At block 22, the green tape piece 34 (FIG. 3) is formed by casting the matrix onto the mylar in a known tape-casting method and cutting the pieces to size. At block 24, after the mylar is removed, the tape piece 34 is laminated to the sensor body 32 (FIG. 3) along with a non-porous tape piece 30 of a known type using the iso-static lamination process described above. At block 26, the sensor body 32 and green tapes 30, 34 are co-sintered as described herein. The porous tape piece 34 covers the gas-sensing portion of the electrolyte of the sensor 32 and the non-porous tape piece 34 covers the rest of the same side of the electrolyte of the sensor 32. The result is the sensor body with the porous ceramic as described herein as a protective coating.

As described herein, the relative proportions of the high and low reactivity powders are adjusted to match the shrinkage of the tape to the shrinkage of electrolyte. The shrinkages are said to "match" when the resultant laminated structure, when fired, maintains its flat shape. It has been found that for an electrolyte substrate 4.82 mm wide that shrinks 17% when fired alone, a 4.82 mm wide porous tape that shrinks approximately 14% when fired alone will, when laminated to the electrolyte, yield a flat structure when fired. When the electrolyte substrate is 7.23 mm wide, a 7.23 mm wide porous tape that shrinks approximately 16.5% when fired alone will, when laminated to the electrolyte, yield a flat structure when fired. For other electrolyte substrate sizes, simple experimentation can determine the best shrinkage of the porous coating to properly match that of the electrolyte so that the tape and electrolyte together, when fired, yield a flat structure.

EXAMPLE 11

According to an example implementation of this invention, the porous ceramic coating provides a diffusion barrier of the type useful on wide-range oxygen sensors to limit the rate of oxygen diffusion to or from an electrolyte body. To form the diffusion barrier, the low reactivity powder was provided at 1 part for every 1.5 parts of the high reactivity powder, with the carbon black providing 10% of the volume of the total volume of the powders. The green body using the powders of this example was co-sintered over the negative electrode of a solid electrolyte cell.

Figure 4:
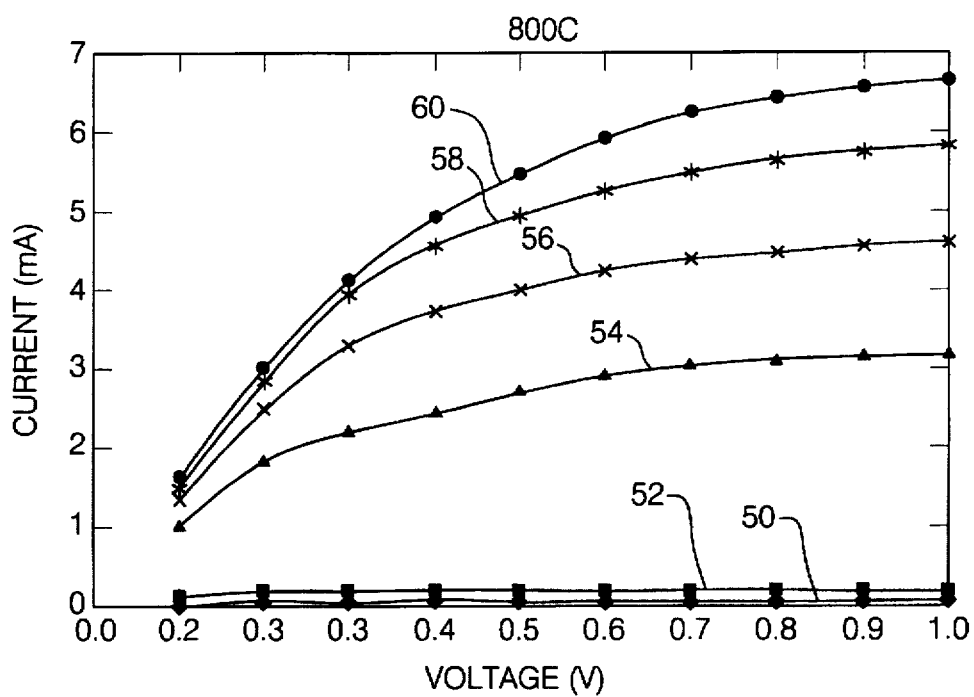
FIGS. 4 and 5 illustrate diffusion characteristics of an example porous ceramic substrate according to this invention.

Referring to FIG. 4, electrical current was measured through the electrolyte cell responsive to a potential applied to the cell in 0.1 volt increments. This was done in atmospheres of various concentrations of oxygen in nitrogen at a temperature of 800° C. Traces 50, 52, 54, 56, 58 and 60 plot the current response of the cell in oxygen concentrations of 200 parts per million (ppm), 1000 ppm, 2%, 3%, 4% and 5%, respectively. The traces illustrate a desirable character of the diffusion barrier: that for a given concentration of oxygen, after the voltage across the cell reaches a certain level, the current through the electrolyte levels off because of the limited rate of oxygen diffusion through the porous ceramic.

Figure 5:
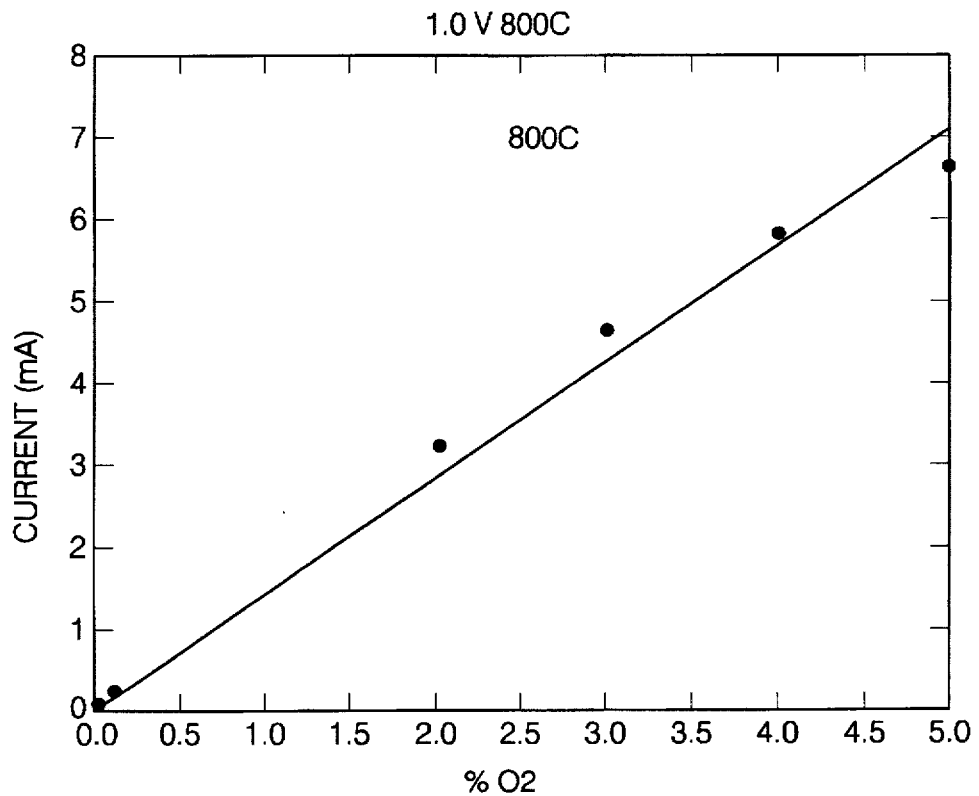

The plot in FIG. 5 was obtained by applying a 1.0 volt potential across the electrolyte cell and measuring the current through the cell as the oxygen percent in a nitrogen atmosphere was increased. The plot illustrates that, as the oxygen concentration increases, the current through the cell increases in a linear manner. Thus FIG. 5 illustrates another desirable characteristic of the diffusion barrier on the electrolyte cell: that, for a given voltage beyond where the current levels off, there is a linear relationship between current and oxygen concentration.

While the example tapes above were fabricated by casting the matrix onto a mylar, this invention applies equally to other forms of tape production, including roll compaction, dry pressing, extrusion, calendering, injection molding and slip casting.

We claim:

1. A process for assembling a porous ceramic coating to a substrate comprising:

forming a ceramic matrix tape including a first ceramic powder having a first full density sintering temperature, a second ceramic powder having a second full density sintering temperature and a fugitive filler material;

placing the ceramic matrix tape onto the substrate; and heating the ceramic matrix tape and substrate to a sintering temperature above the first full density sintering temperature and below the second full density sintering temperature, wherein the fugitive filler material decomposes during said heating.

2. A process for assembling a porous ceramic coating to a substrate according to claim 1, wherein the fugitive filler material has an average particle size of one micron or less.

3. A process for assembling a porous ceramic coating to a substrate according to claim 1, wherein relative proportions of the first and second ceramic powders are adjusted to match shrinkage of the ceramic matrix to shrinkage of the substrate.

4. A process for assembling a porous ceramic coating to a substrate according to claim 1, wherein the first ceramic powder comprises zirconia.

5. A process for assembling a porous ceramic coating to a substrate according to claim 1, wherein the second ceramic powder comprises at least one member of a set comprising pre-fired zirconia and alumina.

6. A process for assembling a porous ceramic coating to a substrate according to claim 1, wherein, after the heating, the ceramic matrix tape forms the porous ceramic coating and wherein the porous ceramic coating has a median pore diameter less than one micron.

7. A process for assembling a porous ceramic coating to a substrate according to claim 1, wherein, after the heating, the ceramic matrix tape forms the porous ceramic coating and wherein the porous ceramic coating has a median pore diameter less than 0.5 microns.

8. A process for assembling a porous ceramic coating to a substrate according to claim 1, wherein an independent shrinkage of the ceramic matrix tape is less than an independent shrinkage of the substrate.

9. A process for producing a porous ceramic comprising:

providing a first ceramic powder having a first full density sintering temperature;

providing a second ceramic powder having a second full density sintering temperature;

providing a fugitive filler material;

forming a green body from the first ceramic powder, the second ceramic powder and the fugitive filler material; and heating the green body to a temperature between the first and second full density sintering temperatures.

10. A process for assembling a porous ceramic coating to a substrate comprising:

forming a ceramic matrix tape including a first partially stabilized ceramic powder having a first full density sintering temperature, a second partially stabilized ceramic powder having a second full density sintering temperature and a fugitive filler material;

placing the ceramic matrix tape on the substrate; and heating the ceramic matrix tape and substrate to a sintering temperature above the first full density sintering temperature and below the second full density sintering temperature, wherein the fugitive filler material decomposes during said heating and wherein, after the heating, the ceramic matrix tape forms the porous ceramic coating for the substrate.

* * * * *